United States Patent
Wu et al.

(10) Patent No.: US 7,138,423 B2
(45) Date of Patent: Nov. 21, 2006

(54) ARYLPYRROLIDINE DERIVATIVES AS NK-1 /SSRI ANTAGONISTS

(75) Inventors: Yong-Jin Wu, Madison, CT (US); Huan He, Tallahassee, FL (US); Joanne J. Bronson, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/183,702

(22) Filed: Jul. 18, 2005

(65) Prior Publication Data

US 2006/0020011 A1    Jan. 26, 2006

Related U.S. Application Data

(60) Provisional application No. 60/589,677, filed on Jul. 20, 2004.

(51) Int. Cl.
*A01N 43/36* (2006.01)
*A01N 43/38* (2006.01)
*C07D 207/08* (2006.01)
*C07D 209/14* (2006.01)

(52) U.S. Cl. ............ 514/408; 514/413; 514/422; 548/518; 548/469; 548/560; 548/577

(58) Field of Classification Search ......... 514/408, 514/414; 548/470
See application file for complete search history.

(56) References Cited

U.S. PATENT DOCUMENTS 6,136,824 A    10/2000    MacLeod et al.

FOREIGN PATENT DOCUMENTS

WO    WO 2004/005255    1/2004
WO    WO 2004/005256    1/2004

OTHER PUBLICATIONS

Kramer et al. (1998), Science, 281, 1640.*
Maggi (1995), vol. 26, No. 5, P911 (Abstract).*
Kramer, Mark S., et al., "Distinct Mechanism for Antidepressant Activity by Blockade of Central Substance P Receptors", *Science*, 281 (1998) 1640-1645.

Maubach, Karen A., et al., "Novel Strategies for Pharmacotherapy of Depression", *Current Opinion in Chemical Biology*, 3 (1999) 481-488.
Rosen, Terry J., et al., "Synthesis and Structure-Activity Relationships of CP-122,721, A Second-Generation NK-1 Receptor Antagonist", , *Bioorganic & Medicinal Chemistry Letters*, 8 (1998) 281-284.
Ryckmans, Thomas, et al., "First Dual $NK_1$ Antagonists-Serotonin Reuptake Inhibitors: Synthesis and SAR of a New Class of Potential Antidepressants", *Bioorganic & Medicinal Chemistry Letters*, 12 (2002) 261-264.

* cited by examiner

*Primary Examiner*—Joseph K. McKane
*Assistant Examiner*—Yong Chu
(74) *Attorney, Agent, or Firm*—Aldo A. Algieri

(57) ABSTRACT

The present disclosure relates to chemical compounds and their use in treatment of human diseases. A particular embodiment relates to compounds of Formula (I) or an isomer, a pharmaceutically acceptable salts or solvates thereof or a pharmaceutically acceptable formulation comprising said compounds

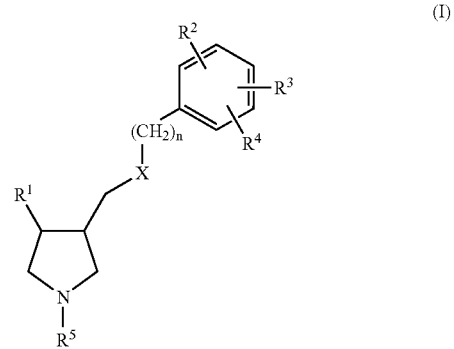

(I)

are useful for the treatment or prevention of conditions mediated by tachykinins and/or selective inhibition of serotonin reuptake transporter protein. The compounds act as dual NK-1 antagonists and selective serotonin reuptake inhibitors.

10 Claims, No Drawings

ARYLPYRROLIDINE DERIVATIVES AS NK-1 /SSRI ANTAGONISTS

CROSS-REFERENCE TO RELATED APPLICATIONS

This is a non-provisional application which claims the benefit of U.S. Provisional Application No. 60/589,677 filed Jul. 20, 2004.

FIELD OF DISCLOSURE

The present application relates to novel chemical compounds and to the use of such compounds in the treatment of various disorders. A particular embodiment relates to arylpyrrolidine derivatives and to pharmaceutical compositions comprising said derivatives useful for the treatment of conditions mediated by tachykinins and/or selective inhibition of serotonin reuptake transporter protein.

BACKGROUND OF THE DISCLOSURE

Depression is a debilitating disease causing significant mortality and affecting up to ten percent of the population. Selective serotonin reuptake inhibitors (SSRI's) have proven to be effective in treating depression, but have the disadvantages of delayed onset of antidepressant activity, limited efficacy and significant side effects. See Novel strategies for pharmacotherapy of depression, K. A. Maubach, N. M. J. Rupniak, M. S. Kramer, and R. G. Hill, *Current Opinion in Chemical Biology* 1999, 3, 491–499. Another class of clinically effective antidepressants are substance P (SP) antagonists which show high affinity and selectivity for the neurokinin 1 (NK-1) receptor. Robust antidepressant activity has been reported for two NK-1 antagonists, MK-869 (M. S. Kramer, et al., *Science* 1998, 281 1640) and CP-122,721 (T. J. Rosen, et al., *Bioorganic and Medicinal Chemistry Letters* 1998, 8, 28 and *CNS Drug News*, Dec. 24, 2000). NK-1 antagonists offer an alternative approach for treating depression in patients that respond poorly to the SSRI's and other available drugs.

The first dual NK-1 antagonists-serotonin reuptake inhibitors were described by Ryckmans et al. (*Bioorganic and Medicinal Chemistry Letters* 2002, 12, 261–264). Ryckmans discloses phenoxy acetamides and phenyl propionamides as NK-1 antagonists and serotonin reuptake inhibitors and the potential of a new generation of antidepressants.

U.S. Pat. No. 6,136,824 discloses piperidinyl-propane-2-derivatives which exhibit both NK-1 receptor antagonism and/or selective serotonin reuptake inhibitor (hereinafter referred to as SSRI) activity.

International Application WO2004/005256 discloses cyclic amine derivatives that exhibit both NK-1 receptor antagonism and/or SSRI activity.

International Application WO2004/005255 discloses N-benzyl-3-phenyl-3-heterocyclic-propionamide compounds as tachykinin and/or serotonin reuptake inhibitors The compounds instantly disclosed have activity as NK-1 antagonists and/or also have activity as selective serotonin reuptake inhibitors and are thus of use in the treatment of conditions mediated by tachykinins and/or selective inhibition of the serotonin reuptake transporter protein. One aspect of the class of compounds of the present disclosure exhibit both NK-1 receptor antagonist and SSRI activity. Thus, novel dual NK-1 antagonists and SSRI inhibitors effective for the treatment of numerous disorders, such as central nervous system disorders, would be advantageous.

SUMMARY

A novel class of compounds are disclosed that are dual NK-1 antagonists and/or serotonin reuptake inhibitors of Formula (I)

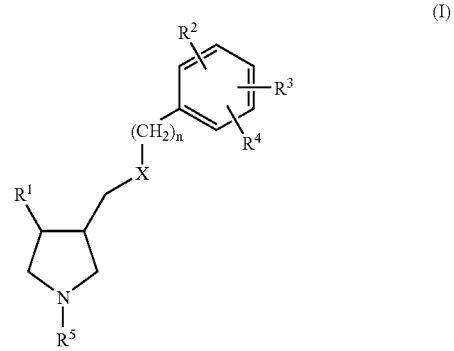

or an isomer, a pharmaceutically acceptable salt or solvate thereof wherein $R^1$ represents phenyl or heteroaryl optionally substituted with hydroxy, $C_{1-6}$ alkyl, fluoro $C_{1-6}$ alkyl, $C_{2-6}$ alkenyl, $C_{1-6}$ alkoxy, cyano, or halogen, in which said heteroaryl is selected from indazolyl, indolyl, thienyl, furyl and pyridyl;

$R^2$, $R^3$ and $R^4$ independently represent H, $C_{1-4}$ alkyl, $C_{1-4}$ alkoxy, fluoro $C_{1-4}$ alkyl, halo or cyano;

X represents O, S, or $NR^6$;

n is 0 or 1; and $R^5$ and $R^6$ are independently H, $C_{1-5}$ alkyl, $C_{3-6}$ cycloalkyl, $C_{3-6}$ cycloalkyl $C_{1-3}$ alkyl.

These compounds antagonize NK-1 receptors, that is; they bind to the receptors such that Substance P and other tachykinins are inhibited from binding to the NK-1 receptors. The compounds are useful as therapeutic agents in conditions characterized by excessive Substance P and other tachykinins expression, and thus, this disclosure provides methods of treating a subject afflicted with such a disorder. The present compounds are also useful as selective inhibitors of serotonin reuptake transporter protein.

DETAILED DESCRIPTION

The compounds of the present disclosure are useful in the treatment of central nervous system disorders and a myriad of other conditions by virtue of their activity as NK-1 receptor antagonists and/or their activity as selective serotonin reuptake inhibitors.

A compound of formula (I) or an isomer, a pharmaceutically acceptable salt or solvate thereof is provided:

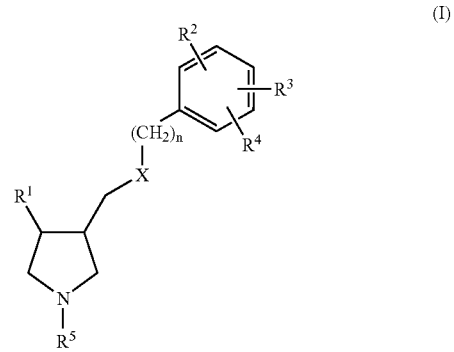

wherein $R^1$ represents phenyl or heteroaryl optionally substituted with hydroxy, $C_{1-6}$ alkyl, fluoro $C_{1-6}$ alkyl, $C_{2-6}$ alkenyl, $C_{1-6}$ alkoxy, cyano, or halogen, in which said heteroaryl is selected from indazolyl, indolyl, thienyl, furyl and pyridyl; $R^2$, $R^3$ and $R^4$ independently represent H, $C_{1-4}$ alkyl, $C_{1-4}$ alkoxy, fluoro $C_{1-4}$ alkyl, halo or cyano; X represents O, S, or $NR^6$; n is 0 or 1; and $R^5$ and $R^6$ are independently H, $C_{1-5}$ alkyl, $C_{3-6}$ cycloalkyl, $C_{3-6}$ cycloalkyl $C_{1-3}$ alkyl.

"Alkyl" means saturated carbon chains, branched or unbranched having the specified number of carbons. The term "$(C_x–C_y)$ alkyl" where x and y are integers means an alkyl group having from x to y carbon atoms. The term "$C_1$ to $C_4$ alkyl" means an alkyl group having from 1 to 4 carbon atoms and includes, without limitation groups such as methyl, ethyl, n-propyl, isopropyl, methylpropyl, n-butyl, t-butyl, isobutyl and sec-butyl. Derived expressions such as $C_{1-4}$ alkoxy are to be construed accordingly.

"$C_{2-6}$ alkenyl" refers to straight-chained and branched alkenyl groups containing from 2 to 6 carbon atoms. Typical examples include vinyl, allyl, dimethylallyl and butenyl groups.

The term "$C_{3-6}$ cycloalkyl" as used herein means a carbon cyclic ring system having from 3 to 6 carbon atoms and includes cyclopropyl, cyclobutyl, cyclopentyl, cyclohexyl and the like. The term "fluoro $C_{1-4}$ alkyl" means a $C_{1-4}$ group in which one or more (in particular 1–3) hydrogen atoms have been replaced by fluorine atoms and includes without limitation trifluoromethyl, fluoromethyl, trifluoromethylethyl, trifluoromethylpropyl and the like.

"Fluoro $C_{1-6}$ alkyl or fluoro $C_{1-4}$ alkyl" means a $C_{1-6}$ or $C_{1-4}$ group in which one or more (in particular 1–3) hydrogen atoms have been replaced by fluorine atoms, "Halo" or "halogen" as used herein includes fluorine, chlorine, bromine, and iodine.

References hereinafter to a compound according to the present disclosure include both compounds of formula (1) and their pharmaceutically acceptable salts and solvates. The solvates may for example be hydrates.

In one embodiment of formula (I), $R^1$ is unsubstituted phenyl or phenyl substituted with fluoro$C_{1-6}$alkyl.

—O—, —S—, $NR^6$ are suitable identities for X, but X is preferably —O—.

n is preferably 0 or 1.

$R^5$ and $R^6$ are preferably H.

$R^2$ and $R^3$ are preferably $CF_3$.

$R^4$ is preferably H.

In another embodiment, $R^2$ and $R^3$ are preferably $CH_3$ and are individually in the meta position with respect to —$CH_2X$. In this embodiment, $R^4$ is preferably H.

In yet another embodiment, $R^2$ and $R^3$ are each $CF_3$ and are individually in the meta position with respect to —$CH_2X$. In this particular embodiment $R^4$ is H.

According to still yet another embodiment, $R^2$ is $CF_3$ and $R^3$ and $R^4$ are each H.

Specific compounds of the present disclosure are:

Trans-3-((3,5-bis(trifluoromethyl)benzyloxy)methyl)-4-phenylpyrrolidine hydrochloride;

Trans-3-((3,5-dimethylbenzyloxy)methyl)-4-phenylpyrrolidine;

Trans-3-((3,5-difluorobenzyloxy)methyl)-4-phenylpyrrolidine;

Trans-3-((2-trifluoromethylbenzyloxy)methyl)-4-phenylpyrrolidine;

Trans-3-((3-trifluoromethylbenzyloxy)methyl)-4-phenylpyrrolidine;

Trans-3-(4-((3,5-bis(trifluoromethyl)benzyloxy)methyl)pyrrolidin-3-yl)-1H-indole;

Trans-3-((3,5-bis(trifluoromethyl)phenoxy)methyl)-4-phenylpyrrolidine trifluoroacetic acid salt; and Trans-3-(4-((3,5-bis(trifluoromethyl)phenoxy)methyl)pyrrolidin-3-yl)-1H-indole;

and pharmaceutically acceptable salts and solvates thereof.

As the compounds of the present disclosure possess asymmetric carbon atoms, the present invention includes all "isomers" which means all possible stereoisomer, geometric isomers, diastereoisomers, enantiomers, anomers and optical isomers of the compounds of Formula I as described herein and in the claims. The use of a single designation such as (R) or (S) is intended to include mostly one stereoisomer at the position indicated. The compounds of the present disclosure contain disubstituted carbon-carbon bond as part of the cyclic ring structure, the present compounds exist in either of two geometric isomeric forms, namely as cis or trans isomers. Preferred are the trans isomers in which the group $R^1$ and the $CH_2X$ group are trans to each other. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The possible enantiomeric forms may also be separated by fractionation through chiral high pressure liquid chromatography columns.

The compounds may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds may be hydrated or non-hydrated.

By virtue of their activity as tachykinin (especially NK-1 receptor) antagonists, the compounds of formula (I) are of value in the treatment of a wide variety of clinical conditions which are characterized by the presence of an excess tachykinin, in particular, substance P activity.

As previously stated, the instantly recited compounds are useful in the treatment of central nervous system disorders, particularly in the treatment or prevention of depression and/or in the treatment of anxiety.

Depression includes, but, is not limited to Major Depressive Disorders (MDD), including bipolar depression, unipolar depression, single or recurrent major depressive episodes, recurrent brief depression, catatonic features, melancholic features including feeding disorders, such as anorexia, weight loss, atypical features, anxious depression, or postpartum onset.

Other central nervous system disorders encompassed within the term MDD include neurotic depression, post-traumatic stress disorders (PTSD) and social phobia; dementia of the Alzheimer's type, with early or late onset, with depressed mood; vascular dementia with depressed mood; mood disorders and tolerance induced by drugs such as alcohol, amphetamines, cocaine, inhalants, opioids, sedatives, anxiolytics and other substances; schizoaffective disorder of the depressed type; and adjustment disorder with depressed mood.

These compounds are also useful in the treatment or prevention of schizophrenic disorders including paranoid schizophrenia, disorganized schizophrenia, catatonic schizophrenia, undifferentiated schizophrenia, residual schizophrenia.

The term anxiety includes, but is not limited to disorders, such as panic disorders, agoraphobia, phobias, obsessive-compulsive disorder, stress disorders including post-traumatic stress disorders, generalized anxiety disorders, acute stress disorders and mixed anxiety-depression disorders.

Compounds of the disclosure are also useful in the treatment or prevention of the cognitive disorders. Cognitive disorders include dementia, amnesia disorders and cognitive disorders not otherwise specified.

Furthermore, compounds of the disclosure are also useful as memory and/or cognition enhancers in healthy humans with no cognitive and/or memory deficit.

In addition, the instantly recited compounds are useful as analgesics. In particular, they are useful in the treatment of traumatic pain such as postoperative pain; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain; pain of bodily origin; gastrointestinal pain; sport's injury pain; dysmennorrhoea; menstrual pain; meningitis; musculoskeletal pain; low back pain e.g. spinal stenosis; prolapsed disc; sciatica; angina; ankylosing spondyolitis; gout; burns; scar pain; itch and thalamic pain such as post stroke thalamic pain.

Compounds of the disclosure are also useful in the treatment of sleep disorders including insomnia, sleep apnea, narcolepsy, and circadian rhymic disorders.

Compounds of the present disclosure are also useful as anti-inflammatory agents. In particular, they are useful in the treatment of inflammation in asthma, influenza and chronic bronchitis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

The instantly recited compounds are also useful in the treatment of allergic disorders, in particular allergic disorders of the skin such as urticaria, and allergic disorders of the airways such as rhinitis.

Compounds of the disclosure are also useful in the treatment of emesis, i.e. nausea, retching and vomiting. Emesis includes acute, emesis and anticipatory emesis. The compounds of the disclosure are useful in the treatment of emesis however induced. For example, emesis may be induced by drugs such as cancer chemotherapeutic agents such as alkylating agents, e.g. cyclophosphamide and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, heartburn, such as episodic heartburn, nocturnal heartburn, and meal-induced heartburn, dyspepsia and functional dyspepsia.

The compounds are also useful in premenstrual dysphoric disorder (PMDD), in chronic fatigue syndrome and multiple sclerosis.

The present disclosure therefore provides a compound of formula (I) or a pharmaceutically acceptable salt or solvate thereof for use in therapy, in particular in human medicine.

There is also provided the use of a compound of formula (1) or a pharmaceutically acceptable salt or solvate thereof in the treatment of conditions mediated by tachykinins (including substance P and other neurokinins) and/or by selective inhibition of the serotonin reuptake transporter protein.

In a further aspect there is provided the use of a compound of formula (I) or a pharmaceutically acceptable salt or solvate thereof in the preparation of a medicament for use in the treatment of central nervous system disorders, such as depression and/or anxiety.

In an alternative or further aspect there is provided a method for the treatment of a mammal, including man, in particular, in the treatment of conditions mediated by tachykinins, including substance P and other neurokinins and/or by selective inhibition of the serotonin reuptake transporter protein comprising administration of an effective amount of a compound of formula (1) or a pharmaceutically acceptable salt thereof.

Another embodiment provides a method for the treatment of a mammal, including man, in particular in the treatment of depression and/or anxiety which method comprises administration of an effective amount of a compound of formula (1) or a pharmaceutically acceptable salt or solvate thereof.

The compounds of the disclosure can be administered in such oral dosage forms as tablets, capsules (each of which includes sustained release or timed release formulations), pills, powders, granules, elixirs, tinctures, suspensions, syrups and emulsions. The compounds may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. The compounds can also be administered in intranasal form by topical use of suitable intranasal vehicles, or by transdermal routes, using transdermal skin patches. When compounds are administered transdermally the dosage will be continuous throughout the dosage regimen.

The dosage and dosage regimen and scheduling of a compound of the present disclosure must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

The instant compounds may be synthesized according to the general schemes provided below. Variables provided in the scheme below are defined in accordance with the description of compounds of the above Formulae unless otherwise specified.

The synthesis of compounds of formula Ia wherein X is O and n is 1 is shown in Scheme 1. The α,β-unsaturated ester 2 underwent cyclization with N-(methoxymethyl)(phenyl)-N-((trimethylsilyl) methyl)methanamine to provide 3. Hydrogenation of 3 under acidic conditions such as hydrochloric acid gave pyrrolidine analog 4, which was protected as the N-Boc derivative 5 by treatment with di-t-butyl dicarbonate in the presence of a base such as triethylamine. Compound 5 was reduced with lithium aluminum hydride to give alcohol 6, which was converted to 7 by treatment with sodium hydride and appropriately substituted benzyl bromide. Deprotection of the Boc group in 7 was achieved under acidic conditions such as hydrogen chloride in ether solution, and the resulting amine 8 was converted to compounds of formula Ia via reductive alkylation with appropriate aldehydes.

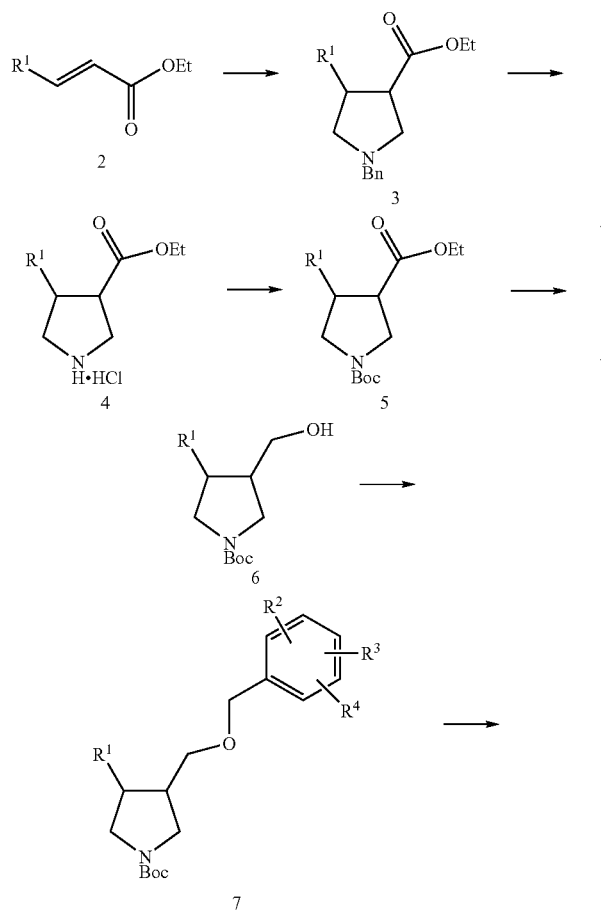

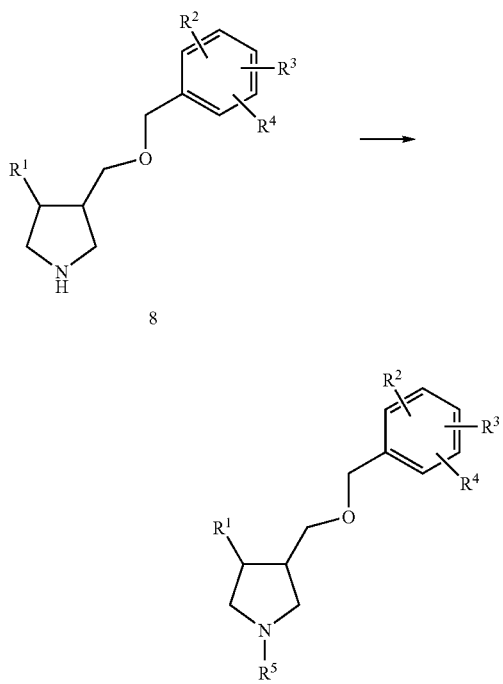

Scheme 2 describes the synthesis of compounds of formula Ib wherein X is oxygen and n is 0. Compounds of formula 6 from Scheme 1 underwent Mitsunobu reaction (O. Mitsunobu, *Synthesis*, 1981, 1) with appropriate phenols to give compounds of formula Ib.

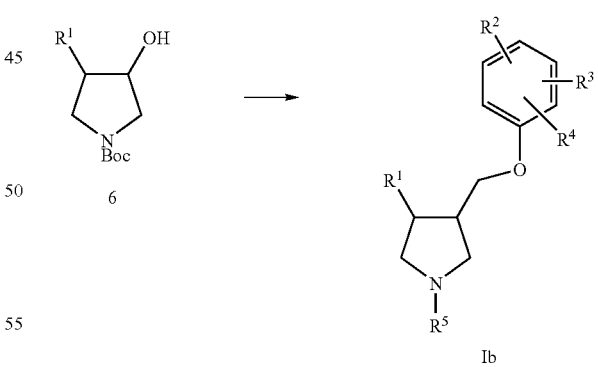

Scheme 3 describes the synthesis of compounds of formula Ic wherein X is NR$^6$. Ester 5 from Scheme 1 was reduced with diisobutylaluminum hydride to furnish aldehyde 10, which underwent reductive alkylation with appropriately substituted benzylamine to provide 11. The conversion of 11 to 9 was carried out in a similar manner to that of 7 to Ib as shown in Scheme 1.

Scheme 3

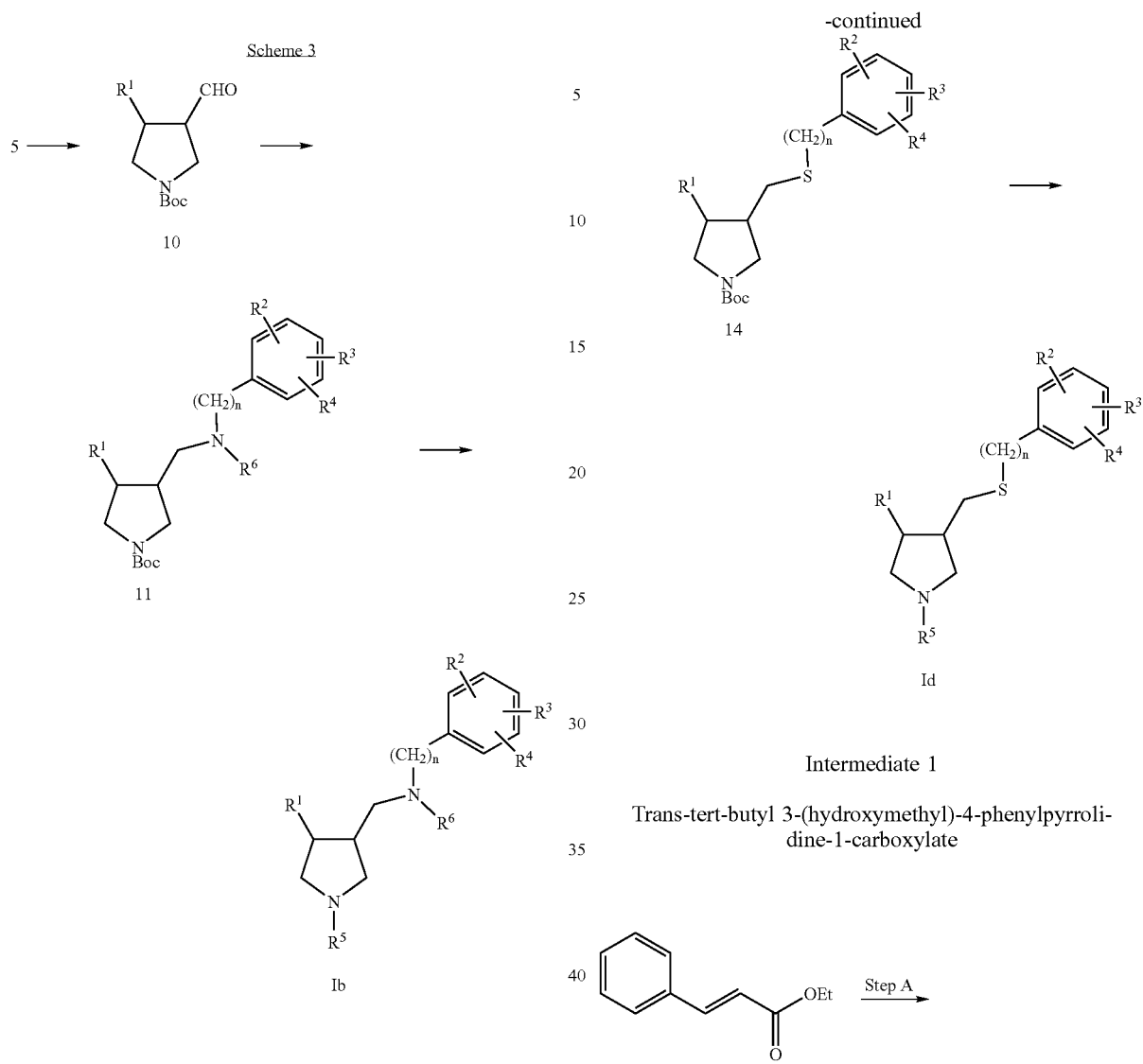

Scheme 4 depicts the synthesis of compounds of formula Id wherein X is sulfur atom. Alcohol 6 from Scheme 1 was converted to 13 wherein L is a mesyl group or tosyl group by treatment with mesyl chloride or tosyl chloride, respectively, in the presence of a base such as triethylamine. Exposure of 13 with appropriately substituted benzylthiol provided compounds of formula 14. The conversion of 14 to 12 was carried out in a similar manner to that of 7 to Id as shown in Scheme 1.

Scheme 3

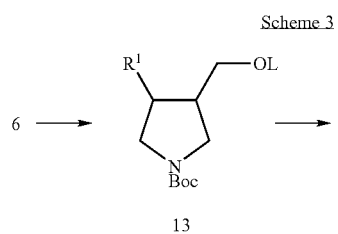

Intermediate 1

Trans-tert-butyl 3-(hydroxymethyl)-4-phenylpyrrolidine-1-carboxylate

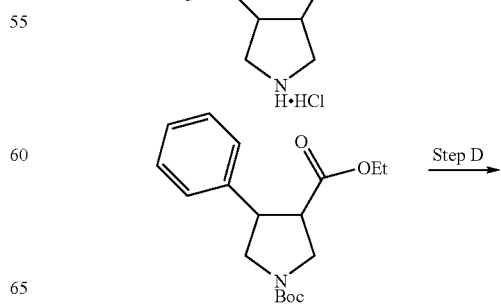

-continued

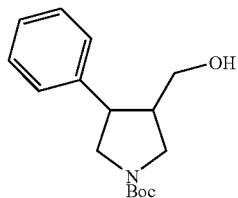

Step A: Trans-ethyl-1-benzyl-4-phenylpyrrolidine-3-carboxylate

To a mixture of ethyl trans-cinnamate (2 g, 11.4 mmol) and N-(methoxymethyl)(phenyl)-N-((trimethylsilyl)methyl)methanamine (2.37 mL) in dichloromethane (18 mL) was added 3 drops of trifluoroacetic acid and the mixture was stirred at 40° C. for 45 min. Then another 0.56 mL of N-(methoxymethyl)(phenyl)-N-((trimethylsilyl) methyl)methanamine and 1 drop of trifluoroacetic acid were added and the mixture was stirred at 40° C. for another 45 min. Then another 0.26 mL of N-(methoxymethyl)(phenyl)-N-((trimethylsilyl)methyl)methanamine and 1 drop of trifluoroacetic acid were added and the mixture was stirred at 40° C. for overnight. After cooling down to room temperature, the mixture was concentrated under vacuum and purified by Flash Chromatography with from 8% ethyl acetate/92% hexane to 10% ethyl acetate/90% hexane over 20 min. to give the title compound as a clear colorless sticky oil (1.69 g, 48% yield). $^1$H NMR (400 MHz, CDCl$_3$) δ 1.20 (3H, t, J=6.4, 9.6 Hz), 2.86 (1H, m), 3.00 (1H, t, J=9.6 Hz), 3.04–3.07 (2H, m), 3.65–3.68 (3H, m), 4.09–4.13 (2H, m), 7.19–7.37 (10H, m). HPLC purity (retention time): 93% (1.30 min, method C). MS: 310.30 (MH$^+$).

Step B: Trans-ethyl-4-phenylpyrrolidine-3-carboxylate hydrochloride

A mixture of trans-ethyl-1-benzyl-4-phenylpyrrolidine-3-carboxylate (1.69 g, 5.47 mmol), concentrated HCl (36% in H$_2$O, 610 mg) and palladium on activated carbon (10 wt %, 169 mg) in ethyl alcohol (27 mL) was put on hydrogenator at 50 psi for overnight. The mixture was filtered through Celite pad and washed with ethyl alcohol. The filtrated was concentrated to give the title compound as a off-white solid (quantitative yield). $^1$H NMR (400 MHz, CD$_3$OD) δ 1.11 (3H, t, J=6.8 Hz), 3.36–3.42 (2H, m), 3.63–3.75 (4H, m), 4.06–4.11 (2H, m), 7.29–7.39 (5H, m). HPLC purity (retention time): 95% (1.05 min, method C). MS: 220.23 (MH$^+$).

Step C: Trans-1-tert-butyl-3-ethyl 4-phenylpyrrolidine-1,3-dicarboxylate

To a mixture of trans-ethyl-4-phenylpyrrolidine-3-carboxylate hydrochloride (5.47 mmol) and di-t-butyl dicarbonate (1.19 g, 5.47 mmol) in dichloromethane (25 mL) was added triethyl amine (2.28 mL) slowly. The mixture was stirred at room temperature overnight and saturated sodium bicarbonate was added to quench the reaction and the organic layer was separated. The aqueous layer was extracted with dichloromethane 2 times and the combined organic layers were dried over magnesium sulfate, filtered and concentrated under vacuum. The crude material was purified by Flash Chromatography with 10% ethyl acetate/90% hexane to give the title compound as a clear colorless sticky oil (1.54 g, 88% yield). $^1$H NMR (400 MHz, CDCl$_3$) δ 1.13 (3H, t, J=7.2 Hz), 1.46 (9H, d, J=6.8 Hz), 3.15 (1H, q, J=9.2 Hz), 3.42 (1H, quintet, J=10.4 Hz), 3.57–3.62 (2H, m), 3.83–3.88 (2H, m), 4.05–4.12 (2H, m), 7.23–7.26 (2H, m), 7.30–7.34 (3H, m). HPLC purity (retention time): 89% (2.04 min, method C). MS: 342.25 (M+Na$^+$).

Step D: Trans-tert-butyl-3-(hydroxymethyl)-4-phenylpyrrolidine-1-carboxylate To a solution of trans-1-tert-butyl-3-ethyl 4-phenylpyrrolidine-1,3-dicarboxylate (823 mg, 2.58 mmol) in diethyl ether (0.6 mL) at 0° C. was added lithium aluminum hydride (1.0 M solution in diethyl ether, 2.58 mL) in dropwise, and the resulting mixture was stirred at 0° C. for 30 min. The reaction was quenched with 2 drops of saturated sodium sulfate and dried over magnesium sulfate, filtered through Celite pad and concentrated in vacuo to give the title compound as clear colorless sticky oil (550 mg, 77% yield). $^1$H NMR (400 MHz, CDCl$_3$) δ 1.45 (9H, d, J=8.8 Hz), 2.45 (1H, m), 3.11 (1H, quintet, J=10 Hz), 3.25–4.00 (3H, m), 3.51–3.43 (1H, m), 3.70–3.78 (2H, m). HPLC purity (retention time): 100% (1.84 min, method C). MS: 300.29 (M+Na$^+$).

INTERMEDIATE 2

Trans-tert-butyl-3-(1-(tert-butoxycarbonyl)-4-(hydroxymethyl)pyrrolidin-3-yl)-1H-indole-1-carboxylate

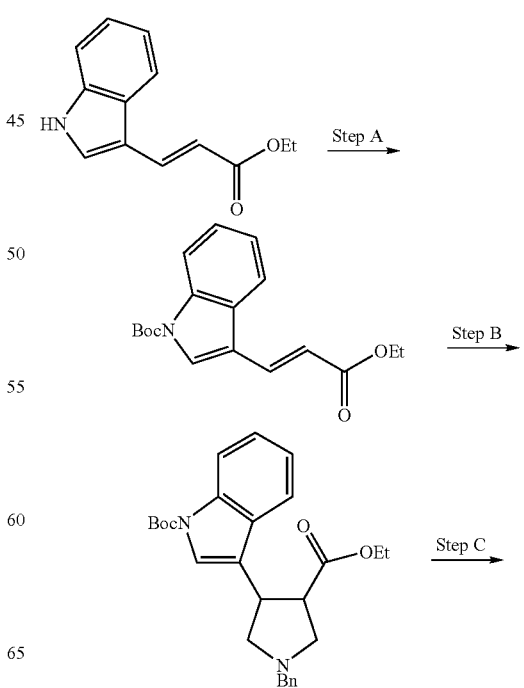

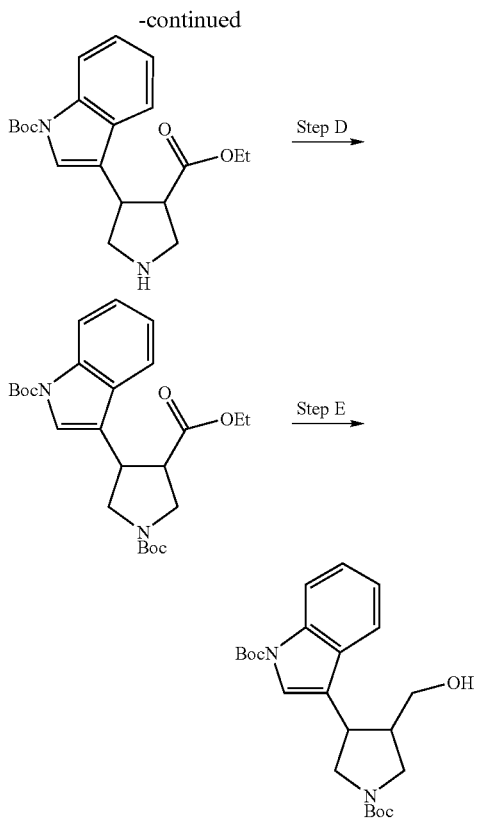

Step A: Trans-tert-butyl 3-(3-ethoxy-3-oxoprop-1-enyl)-1H-indole-1-carboxylate To a mixture of Trans-ethyl 3-(1H-indol-3-yl) acrylate (2.15 g, 10 mmol), DMAP (122 mg) and di-t-butyl dicarbonate (2.20 g, 10.1 mmol) in dichloromethane (20 mL) was added triethyl amine (2.78 mL) slowly. The mixture was stirred at room temperature for 1 hr and saturated sodium bicarbonate was added to quench the reaction and the organic layer was separated. The aqueous layer was extracted with dichloromethane 2 times and the combined organic layers were dried over magnesium sulfate, filtered and concentrated under vacuum. The crude material was purified by Flash Chromatography with from 10% ethyl acetate/90% hexane to 15% ethyl acetate/85% hexane over 20 min. to give the title compound as a yellow sticky oil (2.70 g, 86% yield). $^1$H NMR (400 MHz, CDCl$_3$) δ 1.35 (3H, t, J=7.2 Hz), 1.67 (9H, s), 4.27 (2H, q, J=7.2 Hz), 6.53 (1H, d, J=16 Hz), 7.35 (2H, dt, J=8, 24 Hz), 7.80–7.85 (3H, m), 8.19 (1H, d, J=8 Hz).

Step B: Trans-tert-butyl-3-(1-benzyl-4-(ethoxycarbonyl)pyrrolidin-3-yl)-1H-indole-1-carboxylate To a mixture of trans-tert-butyl 3-(3-ethoxy-3-oxoprop-1-enyl)-1H-indole-1-carboxylate (2.70 g, 8.57 mmol) and N-(methoxymethyl)(phenyl)-N-((trimethylsilyl)methyl)methanamine (2.21 mL) in dichloromethane (11 mL) was added 4 drops of trifluoroacetic acid and the mixture was stirred at 40° C. for 1 hr. Then another 0.15 mL of N-(methoxymethyl)(phenyl)-N-((trimethylsilyl)methyl)methanamine and 2 drop of trifluoroacetic acid were added and the mixture was stirred at 40° C. for another 2 hr. After cooling down to room temperature, the mixture was concentrated under vacuum to give the title compound as a pale yellow sticky oil (quantitative yield). $^1$H NMR (400 MHz, CDCl$_3$) δ 1.21 (3H, t, J=7.2 Hz), 1.65 (9H, s), 2.86 (2H, q, J=8 Hz), 3.03 (1H, t, J=8 Hz), 3.11 (1H, t, J=8 Hz), 3.19 (1H, q, J=8 Hz), 3.70 (2H, dd, J=16 28 Hz), 3.91 (1H, q, J=8 Hz), 4.13 (2H, q, J=8 Hz), 7.20–7.38 (7H, m), 7.45 (1H, s), 7.74 (1H, d, J=8 Hz), 8.10 (1H, brd s). HPLC purity (retention time): 100% (1.84 min, method C). MS: 449.38 (M+Na$^+$).

Step C: Trans-tert-butyl-3-(4-(ethoxycarbonyl)pyrrolidin-3-yl)-1H-indole-1-carboxylate To a solution of trans-tert-butyl-3-(1-benzyl-4-(ethoxycarbonyl)pyrrolidin-3-yl)-1H-indole-1-carboxylate (8.57 mmol) in dichloromethane (16 mL) was added 1-chloroethyl chloroformate (1.11 mL) slowly at 0° C. After addition, the mixture was warmed up to room temperature and stirred for 1 hr then concentrated under vacuum. Ethyl alcohol was added and the mixture was stirred at room temperature for 1 hr. The mixture was concentrated under vacuum to give the crude product as a white solid which was used for next step without further purification.

Step D: Trans-1-tert-butyl-3-ethyl 4-(1-(tert-butoxycarbonyl)-1H-indol-3-yl)pyrrolidine-1,3-dicarboxylate To a mixture of trans-tert-butyl-3-(4-(ethoxycarbonyl)pyrrolidin-3-yl)-1H-indole-1-carboxylate (8.57 mmol) and di-t-butyl dicarbonate (1.89 g) in dichloromethane (40 mL) was added triethyl amine (2.38 mL) slowly. The mixture was stirred at room temperature overnight and saturated sodium bicarbonate was added to quench the reaction and the organic layer was separated. The aqueous layer was extracted with dichloromethane 2 times and the combined organic layers were dried over magnesium sulfate, filtered and concentrated under vacuum. The crude material was purified by Flash Chromatography with from 10% acetone/90% hexane to 15% acetone/85% hexane over 20 min. to give the title compound as a white solid (3.84 g, 98% yield in 2 steps). $^1$H NMR (400 MHz, CDCl$_3$) δ 1.16 (3H, m), 1.47 (9H, d, J=7.6 Hz), 1.66 (9H, s), 3.25 (1H, q, J=8 Hz), 3.49–3.57 (1H, m), 3.62–3.72 (1H, m), 3.76–4.01 (3H, m), 4.10 (2H, m), 7.23–7.32 (2H, m), 7.46 (1H, s), 7.54 (1H, d, J=8 Hz), 8.12 (1H, brd d, J=4 Hz). HPLC purity (retention time): 91% (2.31 min, method C). MS: 481.34 (M+Na$^+$).

Step E: Trans-tert-butyl-3-(1-(tert-butoxycarbonyl)-4-(hydroxymethyl)pyrrolidin-3-yl)-1H-indole-1-carboxylate To a solution of trans-1-tert-butyl-3-ethyl 4-(1-(tert-butoxycarbonyl)-1H-indol-3-yl)pyrrolidine-1,3-dicarboxylate (2.62 g, 5.72 mmol) in diethyl ether (23 mL) at 0° C. was added lithium aluminum hydride (1.0 M solution in diethyl ether, 5.72 mL) dropwise and the resulting mixture was warmed up to room temperature and stirred for 2 hr. The reaction was quenched with 2 drops of saturated sodium sulfate and dried over magnesium sulfate, filtered through Celite pad and concentrated in vacuo. The crude mixture was purified by Flash Chromatography with 20% acetone/80% hexane to give the title compound as a white solid (4.16 g, 80% yield).

EXAMPLE 1

Trans-3-((3,5-bis(trifluoromethyl)benzyloxy)methyl)-4-phenylpyrrolidine hydrochloride

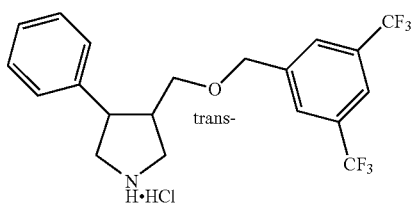

To a solution of trans-tert-butyl-3-(hydroxymethyl)-4-phenylpyrrolidine-1-carboxylate (28 mg) and 3,5-(bis-trifluoromethyl)benzyl bromide (46 mg) in DMF (0.1 mL) at 0° C. was added sodium hydride (95% oil dispersion, 6 mg) and the resulting suspension was stirred at room temperature for 30 min. One drop of H$_2$O was added to quench the reaction and the mixture was dried over sodium sulfate, filtered and concentrated in vacuum. The crude material was purified by preparative TLC eluting with 5% ethyl acetate/95% to give trans-tert-butyl-3-((3,5-bis(trifluoromethyl)benzyloxy)methyl)-4-phenylpyrrolidine-1-carboxylateas as a clear colorless sticky oil (44.3 mg, 76% yield). HPLC purity (retention time): 100% (2.40 min, method C). MS: 526.26 (M+Na$^+$).

The mixture of trans-tert-butyl-3-((3,5-bis(trifluoromethyl)benzyloxy)methyl)-4-phenylpyrrolidine-1-carboxylateas (10 mg) and HCl (1.0 M diethyl ether solution, 0.5 mL) in methanol (0.2 mL) was stirred at room temperature over night. The reaction mixture was concentrated under vacuum to white solid as the title compound (quantitative yield).

$^1$H NMR (CD$_3$OD, 400 MHz) δ 2.77 (1H, m), 3.29 (2H, quintet, J=1.6 Hz), 3.30–3.39 (1H, m), 3.50 (1H, dd, J=8, 12 Hz), 3.60 (1H, dd, J=4, 12 Hz), 3.68–3.73 (2H, m), 4.61 (2H, dd, J=12, 48 Hz), 7.24–7.35 (5H, m), 7.85 (3H, s). HPLC purity (retention time): 98% (1.87 min, method C). MS (ESI) (M+H)$^+$ 404.18.

Examples 2–7 were made in the same manner as illustrated in Example 1.

Examples 8–9 were made in the same manner as shown in Example 1 from trans-tert-butyl-3-(1-(tert-butoxycarbonyl)-4-(hydroxymethyl)pyrrolidin-3-yl)-1H-indole-1-carboxylate (intermediate 2).

| Example | Structure | Name | Appearance/ Form | Ret. Time/ Method | MS (M + H)$^+$ | HPLC purity |
|---|---|---|---|---|---|---|
| 2 | 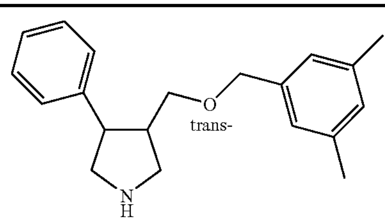 | Trans-3-((3,5-dimethylbenzyloxy)-methyl)-4-phenylpyrrolidine | White solid/ HCl salt | 1.74 min Method C | 296.33 | 100% |
| 3 | 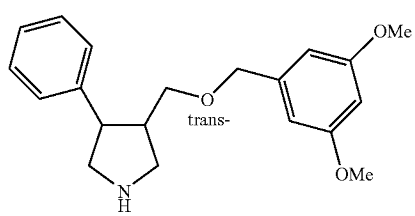 | Trans-3-((3,5-dimethoxybenzyloxy)-methyl)-4-phenylpyrrolidine | White solid/ TFA salt | 1.51 min Method C | 328.31 | 100% |
| 4 | 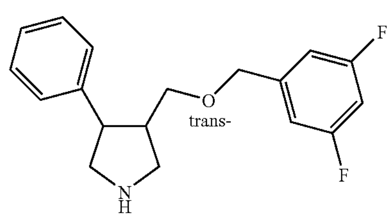 | Trans-3-((3,5-difluorobenzyloxy)methyl)-4-phenylpyrrolidine | White solid/ HCl salt | 1.59 min Method C | 304.26 | 100% |
| 5 | 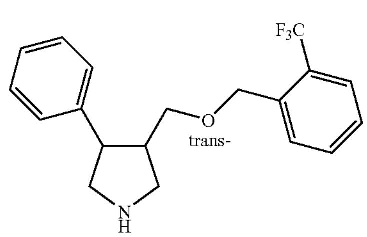 | Trans-3-((2-trifluorobenzyloxy)-methyl)-4-phenylpyrrolidine | White solid/ HCl salt | 1.65 min Method C | 336.24 | 100% |

| Example | Structure | Name | Appearance/ Form | Ret. Time/ Method | MS (M + H)+ | HPLC purity |
|---|---|---|---|---|---|---|
| 6 | 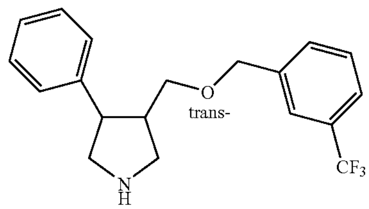 | Trans-3-((3-trifluoromethylbenzyloxy)-methyl)-4-phenylpyrrolidine | White solid/ TFA salt | 1.66 min Method C | 336.25 | 100% |
| 7 | 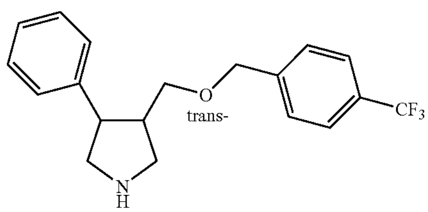 | Trans-3-((4-trifluoromethylbenzyloxy)-methyl)-4-phenylpyrrolidine | White solid/ HCl salt | 1.68 min Method C | 336.31 | 100% |
| 8 | 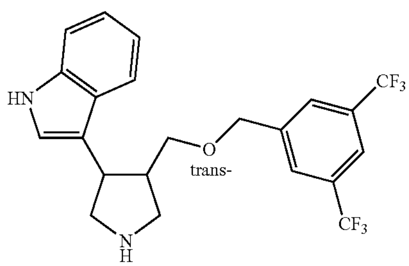 | Trans-3-(4-((3,5-bis(trifluoromethyl)benzyloxy)methyl)pyrrolidin-3-yl)-1H-indole | White solid/ HCl salt | 1.87 min Method C | 443.21 | 98% |
| 9 | 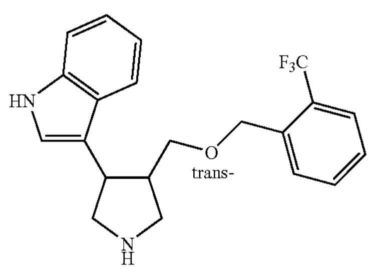 | Trans-3-(4-((2-trifluoromethylbenzyloxy)-methyl)pyrrolidin-3-yl)-1H-indole | White solid/ HCl salt | 1.71 min Method C | 375.20 | 100% |

EXAMPLE 10

Trans-3-((3,5-bis(trifluoromethyl)phenoxy)methyl)-4-phenylpyrrolidine trifluoroacetic acid salt

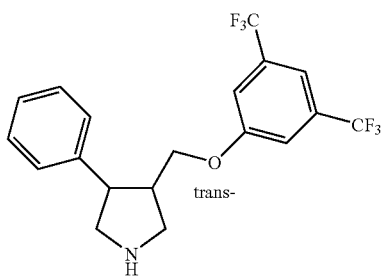

Bis-trifluoromethylphenol (26.1 mg) in THF (0.4 mL) was added to trans-tert-butyl-3-(hydroxymethyl)-4-phenylpyrrolidine-1-carboxylate (28 mg, 0.10 mmol), followed by triphenylphosphine (31 mg, 0.12 mmol) and diethyl azodicarboxylate (20.2 mg, 0.12 mmol). The resulting mixture was stirred at room temperature overnight. The crude material was purified by preparative HPLC to give trans-tert-butyl-3-((3,5-bis(trifluoromethyl)phenoxy)methyl)-4-phenylpyrrolidine-1-carboxylates trifluoroacetic acid salt as a clear colorless sticky oil (31 mg, 50% yield). HPLC purity (retention time): 100% (2.39 min, method C). MS: 512.38 (M+Na+).

The mixture of trans-tert-butyl-3-((3,5-bis(trifluoromethyl)phenoxy)methyl)-4-phenylpyrrolidine-1-carboxylate as trifluoroacetic acid salt (31 mg) and HCl (1.0 M diethyl ether solution, 0.5 mL) in methanol (0.2 mL) was stirred at room temperature over night. The reaction mixture was concentrated under vacuum and purified by preparative HPLC to yield a white solid as the title compound (18 mg, 90% yield).

$^1$H NMR (CD$_3$OD, 400 MHz) δ 2.96 (1H, m), 3.38–3.48 (3H, m), 3.75–3.79 (2H, m), 4.16 (2H, ddd, J=4, 8, 24 Hz), 7.29–7.39 (7H, m), 7.51 (1H, s). HPLC purity (retention time): 98% (1.87 min, method C). MS (ESI) (M+H)+ 390.23.

Example 11 was made using the general procedure shown in Example 10.

EXAMPLE 11

Trans-3-((3,5-dimethylphenoxy)methyl)-4-phenylpyrrolidine hydrochloride

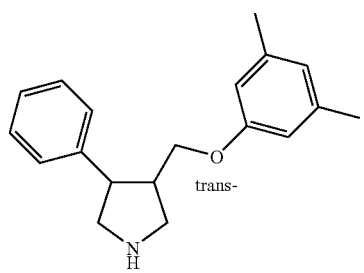

$^1$H NMR (CD$_3$OD, 400 MHz) δ 2.20 (6H, s), 2.84 (1H, m), 3.32–3.48 (3H, m), 3.71–3.76 (2H, m), 3.86 (1H, dd, J=8, 12 Hz), 3.98 (1H, dd, J=4, 12 Hz), 6.45 (2H, s), 6.57 (1H, s), 7.32–7.39 (5H, m). HPLC purity (retention time): 100% (1.71 min, method C). MS (ESI) (M+H)$^+$ 282.32.

Examples 12–13 were made in the same manner as shown in Example 10 from trans-tert-butyl-3-(1-(tert-butoxycarbonyl)-4-(hydroxymethyl)pyrrolidin-3-yl)-1H-indole-1-carboxylate (intermediate 2).

EXAMPLE 12

Trans-3-(4-((3,5-bis(trifluoromethyl)phenoxy)methyl)pyrrolidin-3-yl)-1H-indole

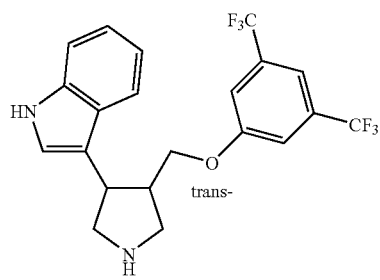

$^1$H NMR (CD$_3$OD, 400 MHz) δ 3.11 (1H, m), 3.45–3.55 (2H, m), 3.78–3.83 (3H, m), 4.22 (2H, ddd, J=4, 8, 24 Hz), 6.99 (1H, t, J=8 Hz), 7.11 (1H, t, J=8 Hz), 7.28 (1H, s), 7.37 (1H, d, J8 Hz), 7.42 (2H, s), 7.50 (1H, s), 7.55 (1H, d, J=8 Hz). HPLC purity (retention time): 99% (1.89 min, method C). MS (ESI) (M+H)$^+$ 429.27.

EXAMPLE 13

Trans-3-(4-((3,5-dimethylphenoxy)methyl)pyrrolidin-3-yl)-1H-indole

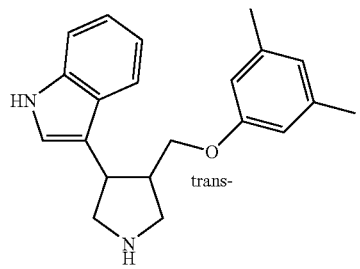

$^1$H NMR (CD$_3$OD, 400 MHz) δ 3.02 (1H, m), 3.43–3.53 (2H, m), 3.73–3.80 (3H, m), 3.98 (1H, dd, J=4, 8 Hz), 4.06 (1H, dd, J=4, 12 Hz), 6.47 (2H, s), 6.56 (1H, s), 6.99 (1H, t, J=8 Hz), 7.11 (1H, t, J=8 Hz), 7.25 (1H, s), 7.37 (1H, d, J=8 Hz), 7.55 (1H, d, J=8 Hz). HPLC purity (retention time): 95% (1.73 min, method C). MS (ESI) (M+H)$^+$ 321.36.

NK-1 Binding Method

U373 cells, a human glioblastoma-astrocytoma cell line that endogenously expresses the neurokinin-1 (NK-1) receptor, were grown in a monolayer culture at 37° C. in 5% CO$_2$ and fed with Minimum Essential Medium (MEM) supplemented with 10% fetal bovine serum. Membranes were prepared as follows: Cells were washed twice with ice-cold phosphate-buffered saline (pH 7.4) and then incubated for 5 to 10 minutes with ice-cold 10 mM Tris buffer (pH 7.4) containing 5 mM EDTA. Cells were removed from plates, homogenized, and centrifuged at 32,000×g for 20 minutes. The resulting supernatant was discarded, and the pellet resuspended by homogenization in 50 mM Tris buffer (pH 7.4) containing 1 mM EDTA and centrifuged at 32,000×g for 20 minutes. The resulting supernatant was discarded, and the pellet resuspended by homogenization in NK-1 binding assay buffer (50 mM Tris-HCL (pH 7.4), 3 mM MnCl$_2$, 200 µg/ml BSA, 5 µg/ml chymostatin, 40 µg/ml bacitracin and 4 µg/ml leupeptin).

On the day of an experiment the membrane preparation was thawed, homogenized and diluted with NK-1 binding assay buffer to the appropriate concentration. Competition binding assays were performed in 96 well plate format by incubating membranes (5–10 ug/well) with Bolton Hunter labeled [$^{125}$I] Substance P, at a concentration of 200 nM, and concentrations of drugs ranging from 10000 to 0.01 nM. Samples were incubated for 30 min at 20° C. then filtered through GF/B glass fiber filters (pretreated with 1% polyethyleneimine and 0.3% Triton X-100) using a Brandel cell harvester. The filters were then washed with 10 ml ice cold 50 mM Tris-HCL (pH 7.4) containing 3 mM MgCl$_2$. Nonspecific was defined in the presence of 2 µM L-733,060 (a non-peptide NK-1 antagonist). Amount of radioligand bound in the presence and absence of competitor was analyzed by plotting (−)log drug concentration versus the amount of radioligand specifically bound. The midpoint of the displacement curve (IC$_{50}$, nM), signifies the potency. K$_i$ values were calculated using the method of Cheng and Prusoff [Cheng, Y.-C. and Prusoff, W. H., *Biochemical Pharmacology*, Vol. 22, pp. 3099–3108, Pergamon Press (1973)].

Serotonin Transporter Binding Assay

HEK-293 cells that stably express human serotonin transporters (HEK-hSERT cells) were grown at 37° C. in 5% $CO_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM $Na_2PO_4$, 1.5 mM $KH_2O_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mmol) and increasing concentrations of test compounds for 1 hr at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 ml of ice-cold Tris wash buffer. Non-specific binding was defined with 10 μM fluoxetine. Amount of radioligand bound in the presence and absence of competitor was analyzed by plotting (−)log drug concentration versus the amount of radioligand specifically bound. The midpoint of the displacement curve ($IC_{50}$, nM), signifies the potency. $K_i$ values were calculated using the method of Cheng and Prusoff [Cheng, Y.-C. and Prusoff, W. H., *Biochemical Pharmacology*, Vol. 22, pp. 3099–3108, Pergamon Press (1973)].

NK-1 binding results are shown below in Table I:

TABLE I

| Example | NK-1 $IC_{50}$ | SERT $IC_{50}$ |
|---|---|---|
| 1 | ** | |
| 2 | * | ** |
| 4 | | ** |
| 5 | | * |
| 6 | | ** |
| 8 | * | |
| 10 | * | ** |
| 11 | | ** |
| 12 | * | |

*** $IC_{50}$ < 20 nM;
** 20 nM < $IC_{50}$ < 100 nM;
* 100 nM < $IC_{50}$ < 300 nM

As shown in Table 1, the compounds of Examples 2 and 10 have activity for both NK-1 and SERT.

What is claimed is:

1. A compound of Formula (I)

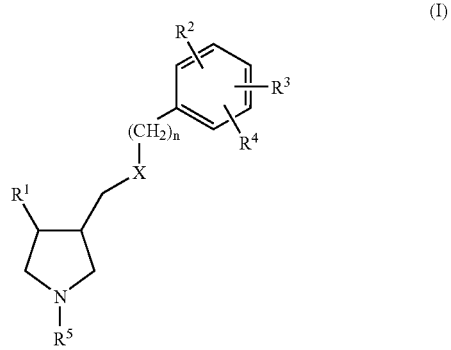

or an isomer, a pharmaceutically acceptable salt or solvate thereof wherein
$R^1$ represents phenyl or heteroaryl optionally substituted with hydroxy, $C_{1-6}$ alkyl, fluoro $C_{1-6}$ alkyl, $C_{2-6}$ alkenyl, $C_{1-6}$ alkoxy, cyano, or halogen, in which said heteroaryl is selected from indazolyl, indolyl, thienyl, furyl and pyridyl;
$R^2$, $R^5$ and $R^4$ independently represent H, $C_{1-4}$ alkyl, $C_{1-4}$ alkoxy, fluoro $C_{1-4}$ alkyl, halo or cyano;
X represents O, or S;
n is 0 or 1; or an
$R^5$ and $R^6$ independently represent H, $C_{1-4}$ alkyl, $C_{3-6}$ cycloalkyl, or $C_{3-6}$ cycloalkyl $C_{1-3}$ alkyl.

2. The compound of claim 1, wherein X is oxygen.
3. The compound of claim 1 wherein $R^1$ is phenyl.
4. The compound of claim 1 wherein $R^1$ is indolyl.
5. The compound of claim 2 wherein $R^2$ and $R^3$ are each $CF_3$ and $R^4$ is H.
6. The compound of claim 5 wherein $R^5$ is H.
7. The compound of claim 6, wherein $R^1$ is phenyl.
8. The compound of claim 7 wherein $R^1$ and —$CH_2X$ group are trans to each other.
9. A pharmaceutical composition comprising a therapeutically effective amount of the compound of claim 1, together with at least one pharmaceutically acceptable excipient.
10. A method for the treatment of depression and/or anxiety which method comprises administration to a patient in need of such treatment a therapeutically effective amount of a compound according to claim 1.

* * * * *